United States Patent
Nandigala et al.

(10) Patent No.: US 10,688,249 B2
(45) Date of Patent: Jun. 23, 2020

(54) MULTIPLE DOSE PHARMACEUTICAL COMPOSITIONS CONTAINING HEPARIN AND/OR HEPARIN-LIKE COMPOUNDS AND DEVICES AND METHODS FOR DELIVERING THE SAME

(71) Applicants: Virchow Biotech Pvt. Ltd., Hyderabad (IN); Virchow Biotech Inc, Arlington, VA (US)

(72) Inventors: Hemanth Nandigala, Hyderabad (IN); Murali Krishna Reddy Tummuru, Hyderabad (IN); Prasad Vure, Hyderabad (IN); Radha Madhavi Dandu, Hyderabad (IN); Chiranjeevi Kondiparthi, Hyderabad (IN)

(73) Assignees: Virchow Biotech Pvt. Ltd., Hyderabad (IN); Virchow Biotech Inc., Arlington, VA (US)

(*) Notice: Subject to any disclaimer, the term of this patent is extended or adjusted under 35 U.S.C. 154(b) by 566 days.

(21) Appl. No.: 15/179,142

(22) Filed: Jun. 10, 2016

(65) Prior Publication Data
US 2016/0361501 A1    Dec. 15, 2016

(30) Foreign Application Priority Data

Jun. 11, 2015 (IN) .......................... 2923/CHE/2015
Jan. 16, 2016 (IN) ............................ 201641001644

(51) Int. Cl.
*A61M 5/315* (2006.01)
*A61K 31/727* (2006.01)
*A61K 31/737* (2006.01)
*A61K 9/00* (2006.01)
*A61M 5/24* (2006.01)

(52) U.S. Cl.
CPC ....... *A61M 5/31593* (2013.01); *A61K 9/0019* (2013.01); *A61K 31/727* (2013.01); *A61K 31/737* (2013.01); *A61M 5/2466* (2013.01)

(58) Field of Classification Search
CPC ........... C08B 37/0075; A61M 5/31593; A61K 31/727
See application file for complete search history.

(56) References Cited

U.S. PATENT DOCUMENTS

| | | | | |
|---|---|---|---|---|
| 5,599,801 | A * | 2/1997 | Branellec | C08B 37/0078 514/56 |
| 6,595,961 | B2 * | 7/2003 | Hetzler | A61L 2/07 604/181 |
| 2004/0248848 | A1 * | 12/2004 | Lensing | A61K 31/7024 514/61 |
| 2005/0020536 | A1 * | 1/2005 | Branellec | A61K 31/7024 514/54 |
| 2007/0287683 | A1 * | 12/2007 | Shriver | C08B 37/0078 514/56 |

\* cited by examiner

*Primary Examiner* — Gerard Higgins
(74) *Attorney, Agent, or Firm* — Fitch, Even, Tabin & Flannery LLP

(57) ABSTRACT

The present invention discloses novel devices, methods, and formulations for multiple dose delivery of an appropriate formulation of Heparin or low molecular weight heparin or a heparin-like compound. Multiple dose formulations of fondaparinux sodium, and preparation methods thereof, are also disclosed.

14 Claims, 8 Drawing Sheets

MULTIPLE DOSE PHARMACEUTICAL COMPOSITIONS CONTAINING HEPARIN AND/OR HEPARIN-LIKE COMPOUNDS AND DEVICES AND METHODS FOR DELIVERING THE SAME

RELATED APPLICATIONS

The present application claims priority from Indian provisional patent application 2923/CHE/2015 filed on Jun. 11, 2015 and Indian provisional patent application 201641001644 filed on Jan. 16, 2016 respectively, both of which are hereby incorporated by reference as if fully set forth herein.

FIELD OF THE INVENTION

The present invention relates to stable compositions and pre-filled devices containing heparin, low molecular weight heparin, or heparin-like compounds, as well as methods of delivering the drug using a device. In particular, the present invention relates to a novel cartridge containing a composition of prefilled heparin or low molecular weight heparin or heparin-like compounds and a method of delivering the drug using said cartridge.

BACKGROUND OF INVENTION

Heparin is a polysaccharide drug with potent anticoagulant activity and is used in the prevention and treatment of thrombosis. It decreases the rate of coagulation by increasing the rate at which anti-thrombin inhibits activated coagulation factors such as thrombin, one of the key enzymes in the coagulation cascade. Certain heparinoids, heparin derivatives, heparin analogues, and other compounds that have heparin-like activity act as anticoagulants. Among all heparin and heparinoids, low molecular weight heparin is of particular interest from a clinical standpoint. Some of the low molecular weight heparins include enoxaparin, ardeparin, dalteparin, or the chemically synthesized heparin-like compound fondaparinux, a pentasaccharide.

Various studies suggest that low molecular weight heparinoids or heparin-like compounds may be associated with reduced risk of bleeding complications, have a longer half-life, and have reduced incidence of thrombocytopenia.

However, it is still difficult to handle low molecular weight heparinoids or heparin-like compounds, since they are fairly large molecules and have prominent negative charges, cannot be administered by oral delivery, and involve invasive delivery approaches. Hence it is necessary to formulate and deliver the drug in a dosage form which is chemically and physically stable to ensure efficacy and adequate patient compliance.

Fondaparinux sodium is a sodium salt form of fondaparinux, a synthetic pentasaccharide having antithrombotic activity. It acts by selectively binding to anti-thrombin III (ATIII), thereby potentiating the neutralization of factor Xa by ATIII. The neutralization of factor Xa interrupts the blood coagulation cascade and thereby inhibits thrombin formation and thrombus development. Fondaparinux does not inactivate thrombin and does not interact with platelet aggregation.

Chemically, fondaparinux sodium is methyl O-2-deoxy-6-O-sulfo-2-(sulfoamino)-α-D-glucopyranosyl-(1→4)-O-β-D-glucopyra-nuronosyl-(1→4)-O-2-deoxy-3,6-di-O-sulfo-2-(sulfoamino)-α-D-glucopyranosyl-(1→4)-O-2-O-sulfo-α-L-idopyranuronosyl-(1→4)-2-deoxy-6-O-sulfo-2-(sulfoamino)-α-D-glucopyranoside, decasodium salt. It has a molecular formula of $C_{31}H_{43}N_3Na_{10}O_{49}S_8$ and a molecular weight of 1728. The structure of fondaparinux sodium is represented by formula I:

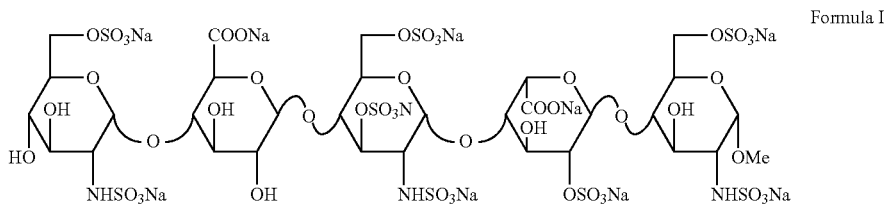

Formula I

Fondaparinux sodium is currently marketed by Mylan Ireland Ltd under the trade name ARIXTRA®. It is available as a sterile, preservative-free injectable solution of fondaparinux sodium for subcutaneous use, in a single dose prefilled syringe. As per the label approved by FDA, ARIXTRA® is indicated for the prophylaxis and treatment of thromboembolic diseases.

Formulations comprising fondaparinux sodium have been proposed in the literature. U.S. Pat. No. 9,089,484 discloses orally administrable pharmaceutical compositions comprising fondaparinux or a pharmaceutically acceptable salt thereof.

US patent application publication no. 20060014698 describes inhalational pharmaceutical compositions comprising fondaparinux.

Single dose formulations of heparin-like compounds such as fondaparinux sodium are available in the form of stable, preservative-free injectable solutions. Currently there are only single dose formulations of fondaparinux, available in the market as ARIXTRA®, provided in glass prefilled syringes. There are no multiple dose formulations of fondaparinux sodium available in the market nor in any form of literature in the public domain.

Prefilled syringes available in the market and used to deliver such products are administered as a unit dose, and may contain preservatives but require proper handling to prevent contamination. However, these syringes may not be capable of multidose administration on account of loss of sterility on first use. Furthermore, it has been noted that the stability and resultant efficacy of the drug product in itself—be it heparin; low molecular weight heparins, or such related molecules—is highly dependent on the nature of the formulation, material of the primary packing material used, and their mutual compatibility. It has been noted that impurity profiles of each of these molecules varies significantly with the change in packaging or container material. In addition, a change in the packaging or container requires extensive studies pertaining to the compatibility of the formulation to that of the packaging or container material. Therefore, it is important to provide the formulation (composition) in a device of appropriate primary packaging material.

SUMMARY OF THE INVENTION

The present inventors have found that an improved treatment may be obtained by administration of periodic, such as daily, individual doses of heparin or heparin-like compounds, using multiple dose cartridges that are convenient to administer, thereby making the administration less cumbersome and more cost effective while improving patient acceptance.

Surprisingly, the inventors of the present application have found that devices in the form of cartridges made of cyclo olefin polymer (COP) for the delivery of multiple dose formulations of low molecular weight heparins or heparin-like compounds, particularly fondaparinux sodium, are more efficient in maintaining the stability and controlling the impurity levels when compared to devices made of glass as evinced with quantitative analysis using high performance liquid chromatography (HPLC). Thus it directs a message to patients that cartridges made of COP are more acceptable and also more advantageous by providing multiple dosages for administration, thus establishing its superiority over prefilled syringes.

In accordance with one aspect of the present invention, the present invention is drawn to a drug delivery device which supplies a measure of a drug.

In an embodiment, the present invention provides a device in the form of a multiple dose cartridge for accurately delivering successive individual dosages of heparins or low molecular weight heparins or heparin-like compounds to patients in need thereof.

In another embodiment, the present invention provides a multiple dose cartridge made of COP for precisely delivering successive individual dosages of heparin or low molecular weight heparin or a heparin-like compound.

In other embodiment, the present invention provides a multiple dose cartridge made of COC for precisely delivering successive individual dosages of heparin or low molecular weight heparin or a heparin-like compound.

In a further embodiment, the present invention provides a device in the form of a multiple dose cartridge made of COP or COC for accurately delivering successive individual dosages of heparin or low molecular weight heparin or a heparin-like compound.

In yet another embodiment, the present invention provides a method for delivery of heparins or low molecular weight heparins or heparin-like compounds using a multiple dose cartridge made of COP or COC.

In a further embodiment, the present invention provides a multiple dose cartridge made of COP for precisely delivering successive individual dosages of heparins or low molecular weight heparins or heparin-like compounds, such that said device is superior in controlling impurities and microbial contamination when compared to a device made of glass.

In one embodiment, the present invention provides sterile, stable, multiple dose pharmaceutical formulations comprising heparins or low molecular weight heparins or heparin-like compounds for parenteral administration to a subject in need thereof. In preferred embodiments of the invention, the heparin-like compound is fondaparinux sodium.

In another embodiment, the present invention provides a sterile, stable, multiple dose pharmaceutical formulation comprising fondaparinux sodium and one or more pharmaceutically acceptable excipients to be filled in cartridges for use in an injection device.

In another embodiment, the present invention provides a multiple dose pharmaceutical formulation comprising fondaparinux sodium and 0.001 to 2% sodium chloride, preferably about 0.9% sodium chloride, in water for injection, to be filled in cartridges for use in a multiple dose injection device.

In yet another embodiment, the present invention provides a multiple dose pharmaceutical formulation comprising fondaparinux sodium and 0.001 to 2% sodium chloride, preferably about 0.9% sodium chloride in water for injection, and one or more pharmaceutically acceptable preservatives, to be filled in cartridges for use in a multiple dose injection device.

In an embodiment of the present invention, the multiple dose pharmaceutical formulation comprises fondaparinux sodium and 0.001 to 2% sodium chloride, preferably about 0.9% sodium chloride in water for injection, and one or more pharmaceutically acceptable antioxidants, to be filled in cartridges for use in a multiple dose injection device.

In a further embodiment, the present invention provides sterile, stable multiple dose pharmaceutical formulations to be filled in cartridges comprising at least about 97% of fondaparinux sodium and other related impurities when quantified by HPLC. In preferred embodiments of the invention, the test formulations of present invention comprise about 98% fondaparinux sodium and other related impurities.

In yet another embodiment, a sterile, stable multiple dose pharmaceutical formulation is provided for subcutaneous administration comprising fondaparinux sodium to be filled in cartridges for use in a multiple dose injection device, wherein Impurity-A, Impurity-B, Impurity-C, Impurity-D, and Impurity-G (described below) are below the level of detection compared to the marketed preparation.

In a further embodiment, the present invention provides methods for preparing sterile, stable, multiple dose pharmaceutical formulations comprising fondaparinux sodium and one or more pharmaceutically acceptable excipients.

In a further embodiment, the present invention provides stable multiple dose formulations comprising fondaparinux or acceptable salts thereof with one or more acceptable excipients and with the provision of an efficient method for accurately parenterally administering individual dosages of a medicament using a device made of COP, such that said formulation is superior in controlling impurity levels when compared to the marketed formulation as evinced with quantitative analysis by HPLC and the device shows superiority in controlling microbial contamination when compared to a device made of glass.

In another embodiment, the present invention provides sterile, stable multiple dose pharmaceutical formulations of fondaparinux sodium filled in cartridges, for the treatment of diseases and conditions in which it is indicated.

The above benefits and various advantages of the several embodiments of the present invention will be more apparent from the following detailed description along with exemplary embodiments and appended figures.

DETAILED DESCRIPTION

Figure 1:
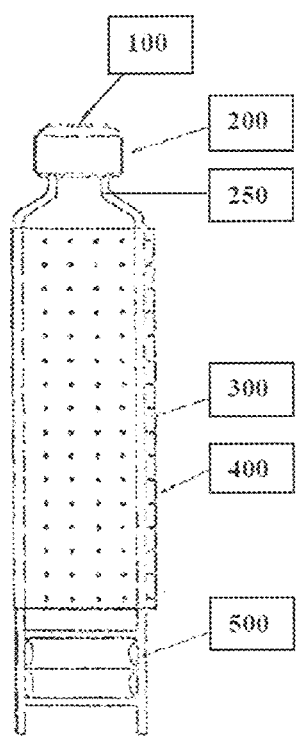
FIG. 1 represents a cross-sectional view of an exemplary cartridge for delivering multiple doses of a drug formulation.
Figure 2:
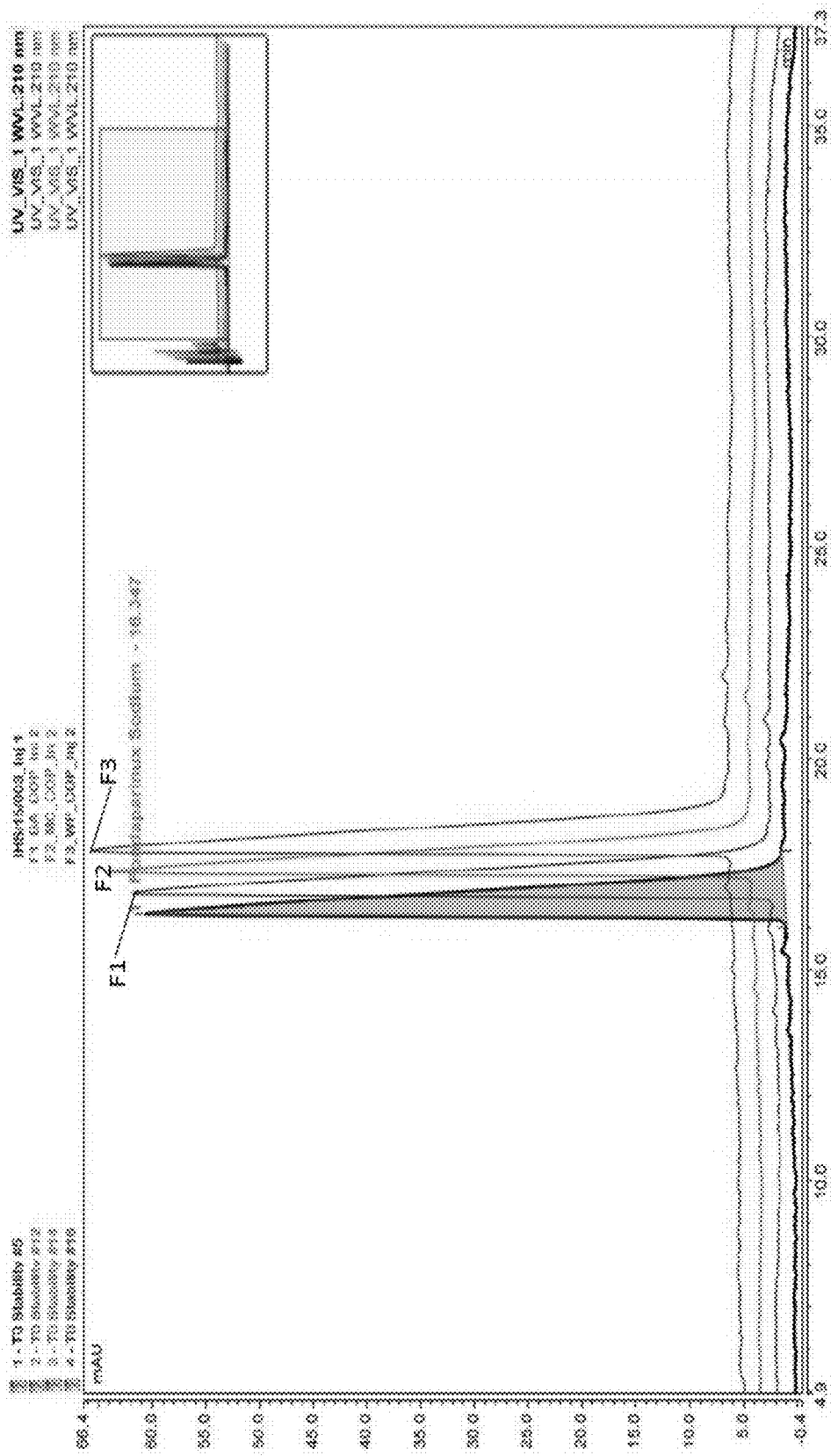
FIG. 2 shows the initial dose assay results of three multi-dose formulations.
Figure 3:
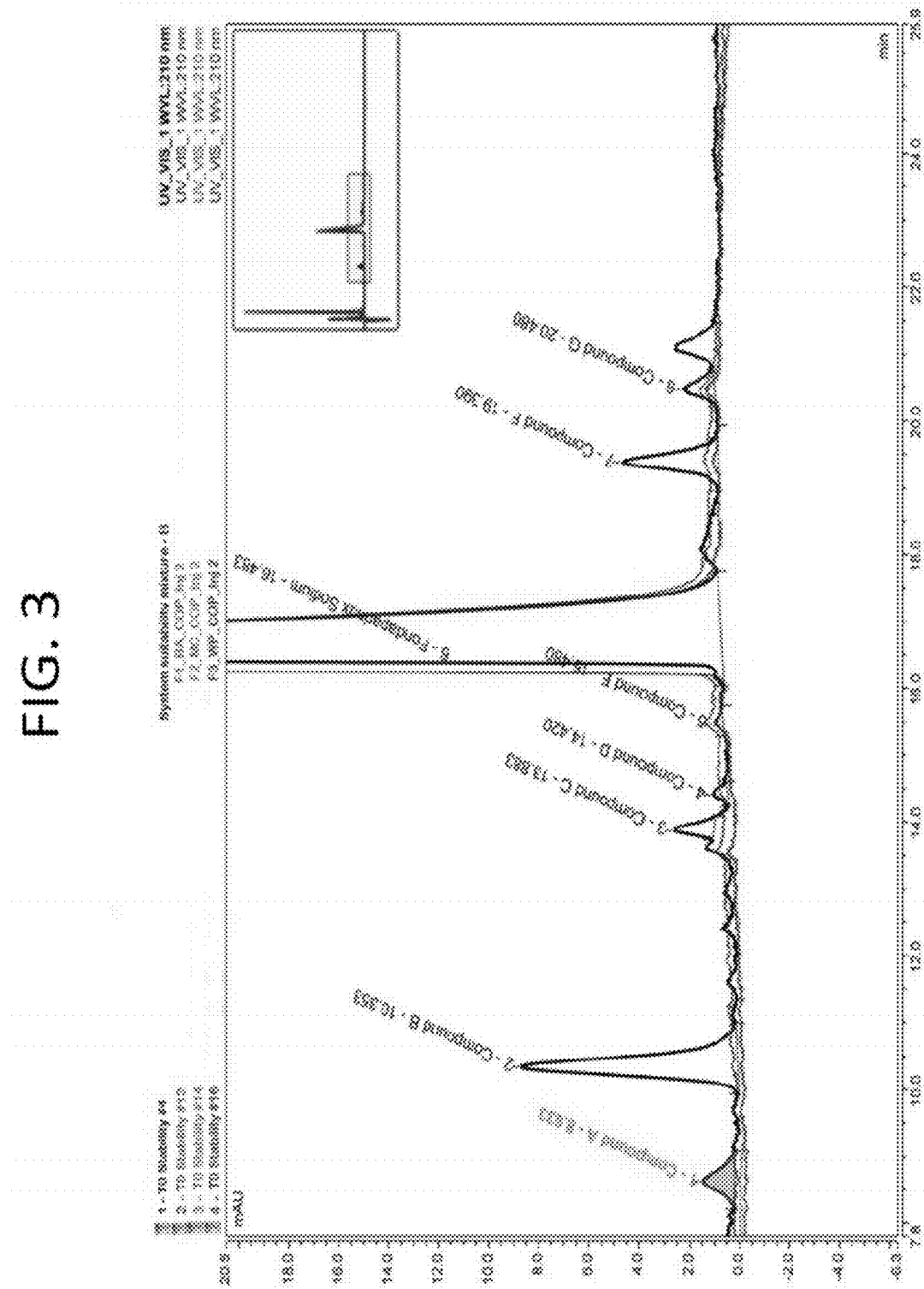
FIG. 3 shows a comparison of inorganic impurities in three multi-dose formulations for an initial dose (day zero).
Figure 4:
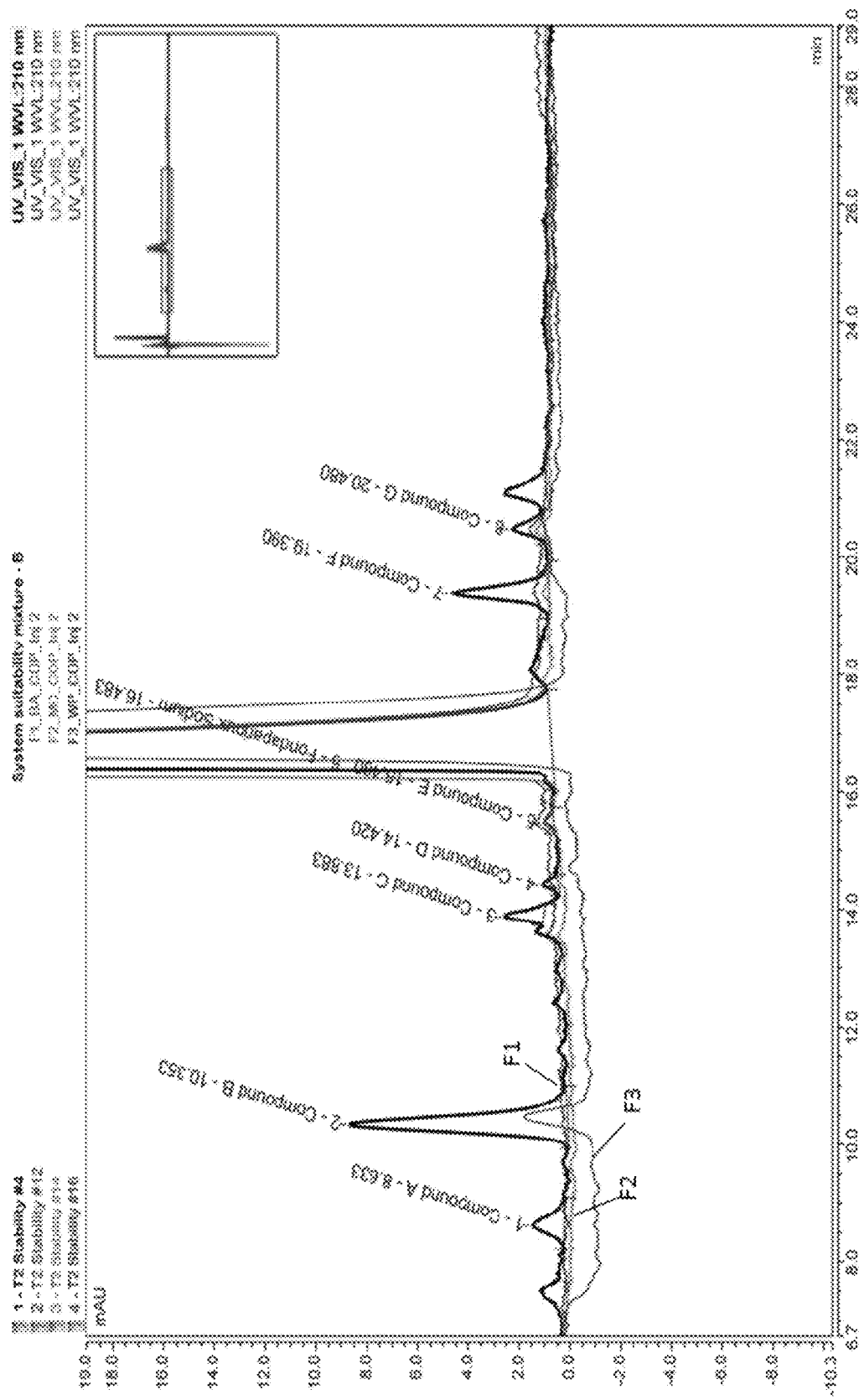
FIG. 4 shows a comparison of inorganic impurities in three multi-dose formulations for a second dose (day two).
Figure 5:
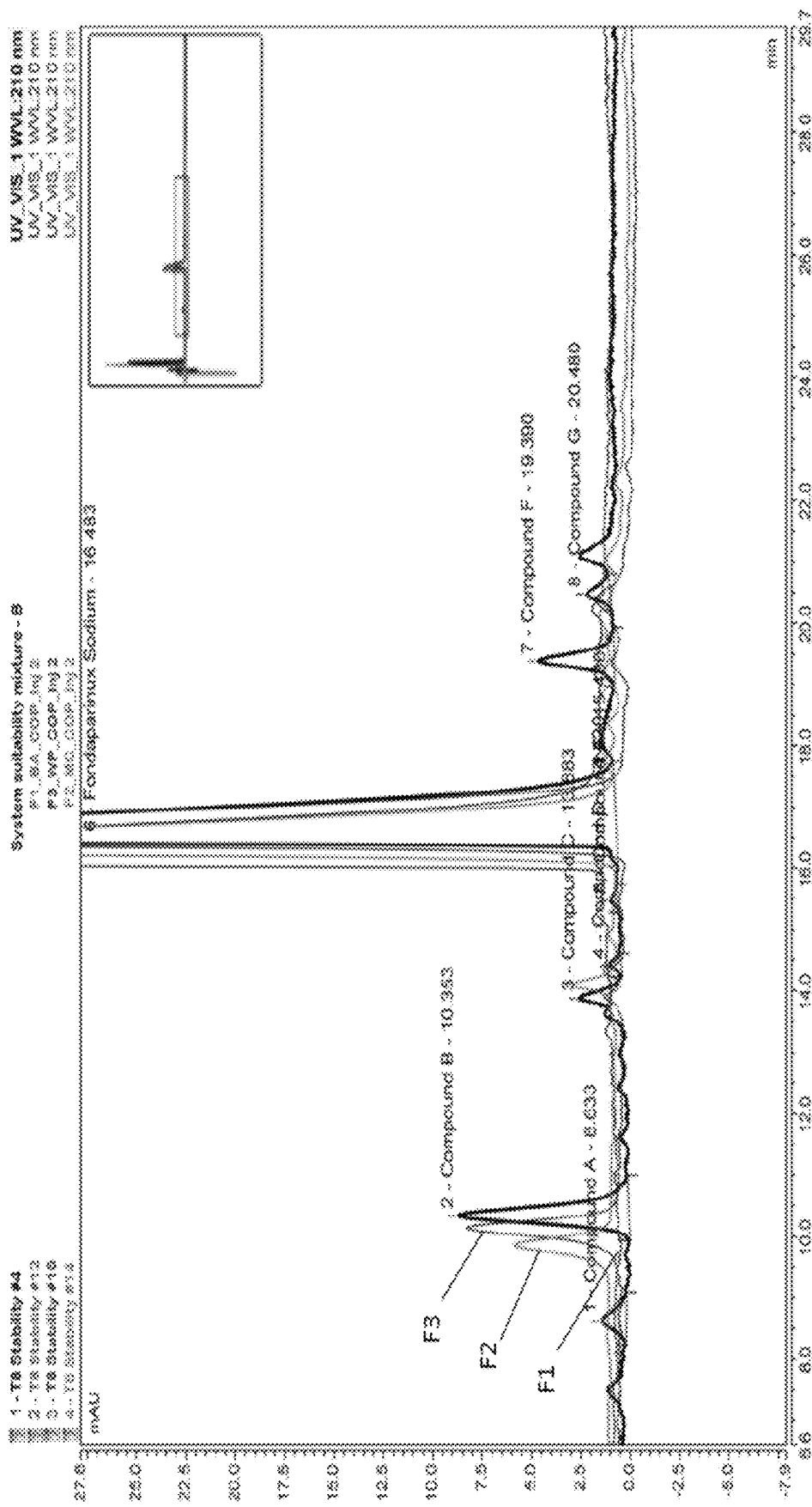
FIG. 5 shows a comparison of inorganic impurities in three multi-dose formulations for an eighth dose (day eight).
Figure 6:
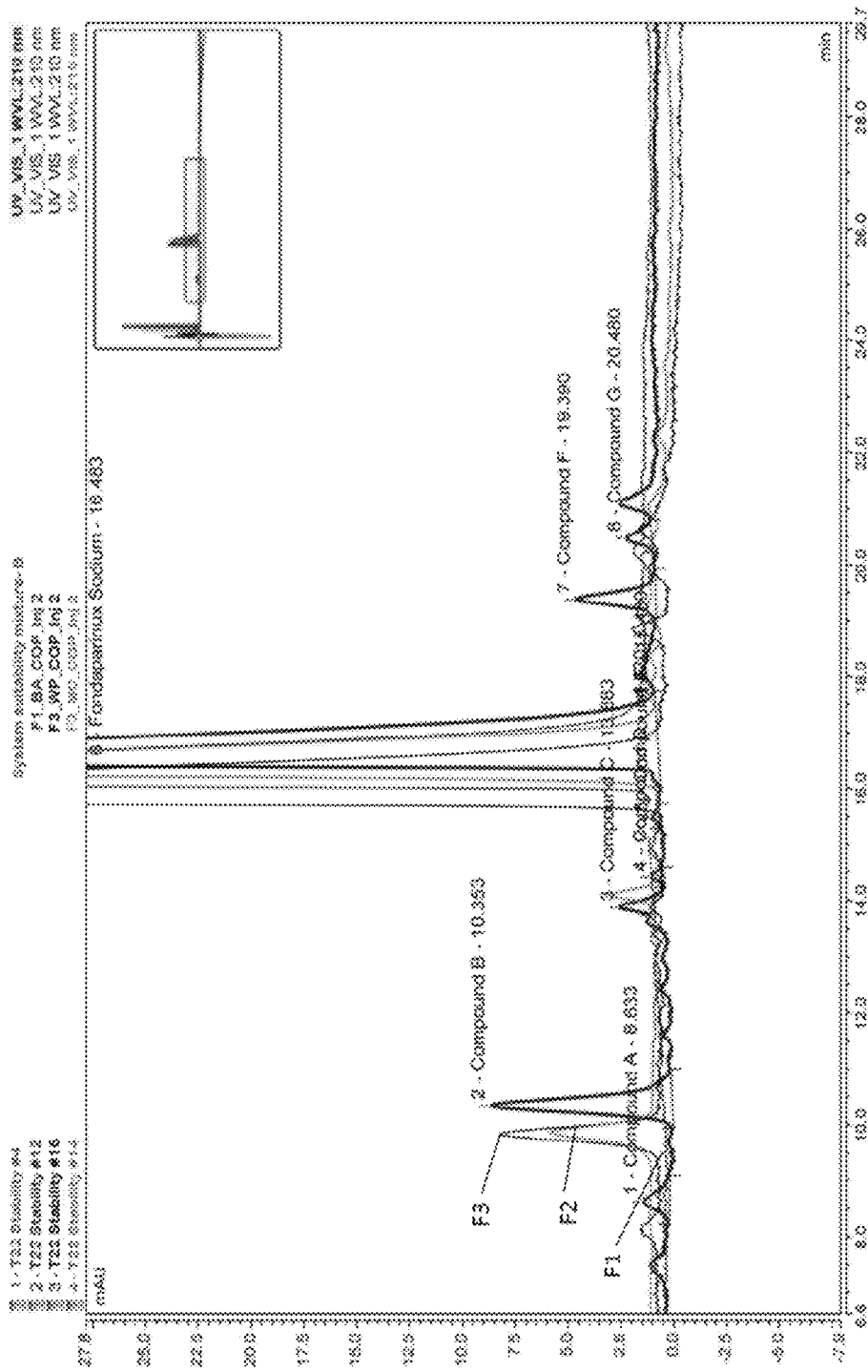
FIG. 6 shows a comparison of inorganic impurities in three multi-dose formulations for a twenty-second dose (day twenty-two).
Figure 7:
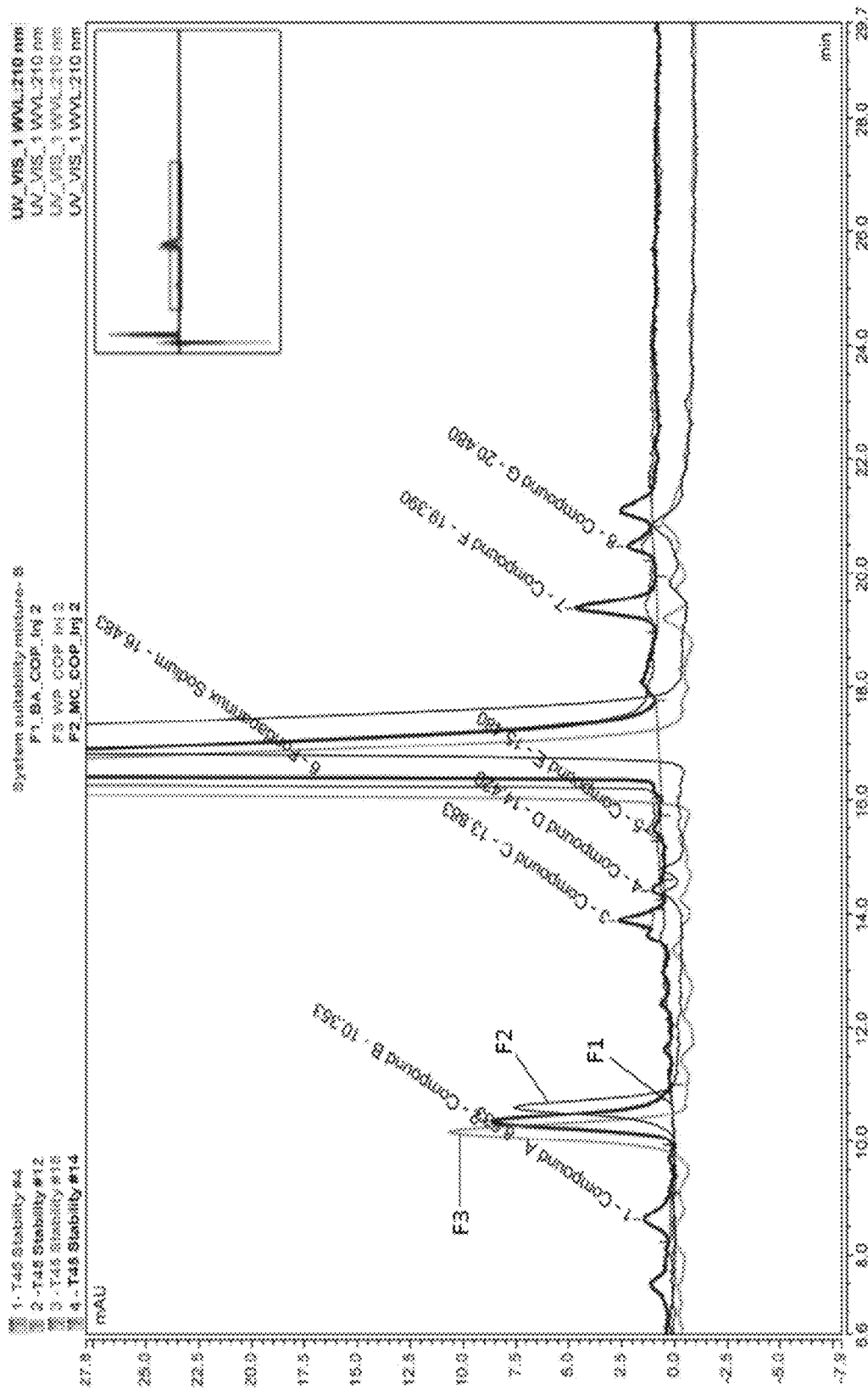
FIG. 7 shows a comparison of inorganic impurities in three multi-dose formulations for a forty-fifth dose (day forty-five).
Figure 8:
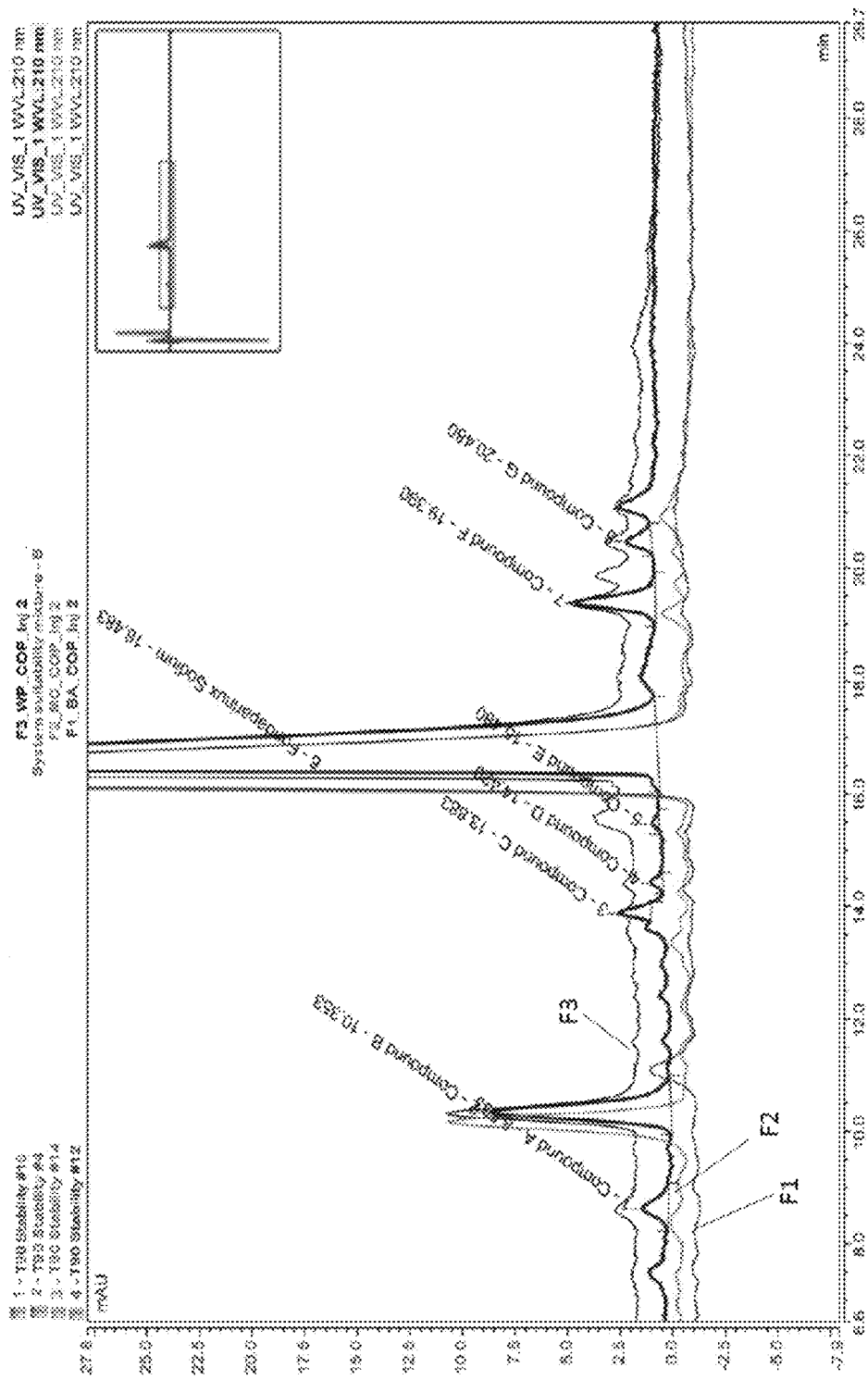
FIG. 8 shows a comparison of inorganic impurities in three multi-dose formulations for a ninetieth dose (day ninety).

The present invention is directed to a device for delivery of Heparin or low molecular weight heparin or a heparin-like compound and a method of delivering such drugs.

Brief Description of Terms

The term "pharmaceutical formulation" as used herein means a product comprising an active pharmaceutical ingredient, together with pharmaceutically acceptable excipients, said pharmaceutical formulation being useful for treating, preventing, or reducing the severity of a disease or disorder by administration of said pharmaceutical formulation to a subject in need thereof. Thus a pharmaceutical formulation is also known in the art as a pharmaceutical composition.

The term "active pharmaceutical ingredient" as used herein refers to low molecular weight heparins, specifically low molecular weight heparins including but not limited to enoxaparin, ardeparin, dalteparin, or a heparin-like compound including but not limited to the chemically synthesized pentasaccharide fondaparinux. The terms "active pharmaceutical ingredient", "medicament", "active agent" or "drug" are used interchangeably.

The term "pharmaceutically acceptable" as used herein means suited for normal pharmaceutical applications, i.e. giving rise to no adverse events in patients.

The term "excipient" or "pharmaceutically acceptable excipient" as used herein means a nontoxic material that is compatible with the physical and chemical characteristics of the active pharmaceutical ingredient and does not interfere with the effectiveness of the biological activity of the active pharmaceutical ingredient, which is generally safe, non-toxic and neither biologically nor otherwise undesirable, and acceptable for veterinary use as well as human pharmaceutical use. An "excipient" or "pharmaceutically acceptable excipient" as used in the specification includes both one and more than one such excipient.

The term "cartridge" as used herein refers to a device for storing and facilitating the delivery of pharmaceutical formulations in multiple doses, for instance in combination with a pen device, double-needle assembly, or other instrument.

The term "parenteral" as used herein refers to a mode of administration of the formulation of present invention usually by injection and includes intravenous, intra-arterial, intramuscular, subcutaneous, intradermal, intraperitoneal, etc.

The term "subject" as used herein refers to an animal, preferably a mammal, including a human or non-human. The terms "patient" and "subject" may be used interchangeably.

The term "treatment" as used herein is defined as the management and care of a patient, e.g. a mammal, in particular a human, for the purpose of combating a disease, condition, or disorder to prevent the onset of the symptoms or complications, or alleviate symptoms or complications, or eliminate a disease, condition, or disorder.

The term "tonicity adjusting agent" as used herein refers to a chemical compound in the pharmaceutical formulation that serves to modify the osmotic pressure of the pharmaceutical formulation such that the osmotic pressure becomes closer to that of human plasma.

The term "antioxidant" as used herein refers to a chemical compound that prevents/minimizes the oxidation of a drug and/or excipients over the shelf life of the product.

Devices

The present invention in one form relates to methods and devices for delivery of any of the low molecular weight heparin or heparin-like compounds identified herein, preferably fondaparinux sodium.

In one embodiment, a cartridge is made of COP or COC glass for accurately delivering successive individual dosages of low molecular weight heparins or heparin like compounds, especially in the form of compositions detailed further herein. In preferred embodiments of the invention, the heparin like compound is fondaparinux sodium.

In even more preferred embodiments, a cartridge is provided for the delivery of multiple dose pharmaceutical formulations of fondaparinux sodium. The cartridges may be provided for use in a multiple dose injection device for subcutaneous administration of formulations as described herein.

In one aspect, the prefilled cartridges are made up of amorphous thermoplastic polymers such as cyclo olefin copolymers (COC) and/or cyclo olefin polymers (COP). Polymers provide improved robustness against breakage and adequate stability against water/gas permeability when compared to glass. COP and COC both are biocompatible and have glass-like optical clarity, low density, excellent moisture barrier capabilities, good mechanical properties, and resistant to aqueous and polar organic media. However, COPs mold with superb transcription, dimensional control and high yield, due to their chemical uniformity and purity. Also, COPs are ductile and less brittle than typical COCs, making them an excellent choice for pharmaceutical drug packaging.

Various embodiments of the present invention may be envisaged within the scope of the present invention. In one embodiment, as shown in FIG. 1, the drug delivery device is housed in a housing unit (400). The housing unit includes a plunger (500) and an area between the plunger and a narrowed neck portion (250) which may be referred to as the drug reservoir area (300).

The housing assembly may be preferably cylindrical in shape with an inner diameter ranging, for instance, from about 12 to about 16 mm, and an outer diameter ranging, for instance, from about 15 to about 18 mm. The housing assembly length may be in the range of, for instance, about 150 to about 175, up to the neck with a wall thickness of, for instance, about 0.25 to about 1.5 mm. Most preferably, the material of the housing assembly is COP.

The housing assembly also includes a plunger (500) and the drug reservoir area (300). The plunger may be placed in such a manner that it has a diameter smaller than that of the housing assembly and is freely moveable inside the assembly. A part of the plunger is found outside the assembly and is moveable with respect to the assembly. The protruding end of the plunger is capable of being held by the end user or otherwise manipulated and the end user is capable of conveniently moving the plunger in a parallel direction to the housing assembly, such that the plunger (500) is capable of compressing the drug present inside the drug reservoir (300) and thereby generating a pressure sufficient to extrude the drug.

The housing assembly includes the drug reservoir (300). The drug reservoir (300) contains a drug which is selected from the group comprising low molecular weight heparins, preferably low molecular weight heparin selected from the group comprising enoxaparin, ardeparin, dalteparin, fondaparinux, most preferably enoxaparin, and fondaparinux. Enoxaparin is obtained by alkaline degradation of heparin benzyl ester, and is administered as a subcutaneous injection. Ardeparin is a partially depolymerized porcine mucosal heparin and is also administered as deep subcutaneous injection. Dalteparin is generally available in single dose prefill syringes and multi dose vials for subcutaneous injections. Fondaparinux is a comparatively new antithrombotic product which retains the advantages of low molecular weight heparins and is produced by chemical synthesis. Most of these products are generally administered subcutaneously or intravenously.

In the embodiment shown in FIG. 1, the drug reservoir leads to a neck portion (250), which leads to an opening. The opening is covered by a cap (200), which is closed by a disc (100). The disc and the cap may be removed and replaced by a needle, or the cartridge may be fitted into a pen device or other instrument including a needle that pierces the disc in order to deliver the drug from the reservoir. Alternatively, the cartridge may be used in any suitable manner amenable for delivery in conjunction with any other device.

In one form, the cartridge may have a moveable rubber type bung or stopper located at one end of the cartridge reservoir. A cap (200) that may include the bung may be covered by a metallic disc (100) which can be removed during administration. The rubber bung or other seal located at one end, often the end containing the neck, may be pierced or removed during administration. The bung may also be held in place by a crimped annular metal band.

The cartridge may be placed in a disposable pen delivery device. The cartridges of the present invention are capable of being permanently placed in non-reusable devices and are also capable of being placed in, removed from, and replaced in reusable devices without destroying the device itself.

Since the cartridges contain a fixed amount of material, these cartridges may be amenable to devices which do not have a resettable dose setting mechanism.

The cartridges of the present invention are also amenable to devices which have a dose setting mechanism. In such an instance, the cartridge is capable of being inserted into a holder or retainer and the cartridge is attached directly to the dose setting mechanism to select the dose.

In one aspect of the present invention, the cartridge of the present invention is capable of being attached to a double ended needle assembly. The needle assembly may be threaded onto, pushed, or snapped on a distal end of the cartridge housing opposite the plunger. In this manner, a double ended needle placed on the assembly penetrates through a pierceable seal, such as a rubber bung, at a distal end of the cartridge. After an injection, the needle assembly may be removed and discarded.

After the drug is exhausted, the user may detach the cartridge housing from the dose setting mechanism and then remove the empty cartridge from the cartridge retainer and replace the empty cartridge with a filled cartridge.

In another embodiment of the present invention, a cartridge is also amenable to a dose setting mechanism by connecting the plunger (500) to the dose setting mechanism.

The present invention also discloses a method of delivering the drug by a cartridge.

Sterility is one of the most important characteristics of parenteral formulations. Various sterilization procedures are well known to the persons skilled in the art. The pharmaceutical formulations disclosed herein may be sterilized using any of the conventional methods such as autoclaving, sterilization by filtration, or by exposing to ionizing radiations. Pharmaceutical formulations may be contained in cartridges or other delivery devices of various materials, such as PVP, PEG, COC, or COP, preferably COP or COC.

Sterility tests have been conducted to evaluate the microbial contamination of pharmaceutical formulations of fondaparinux sodium with and without preservatives, stored in cartridges made of COP or glass, upon multiple opening.

A sterility test was conducted in six cartridges made of glass or COP filled with formulations of fondaparinux sodium stored at appropriate conditions (Room Temperature ("RT") & Refrigerated ("Fridge")) as per (USP 37 (71)) pharmacopeia with testing intervals at '0' hour opening and 24 hour, 72 hours, 5th day, and final 7th day opening.

The observations of the sterility studies are reported in Table 1. Abbreviations used in Table 1 are as follows:

TABLE 1

Microbiological examination of MDCs under study

| S.No | Product studied MDCs | At 0 Hr just after first opening sent for MB-lab | | At 24 Hrs just after second opening sent for MB-lab | | At 72 Hrs just after Third opening sent for MB-lab | | On $5^{th}$ day | | On $7^{th}$ Day | |
|---|---|---|---|---|---|---|---|---|---|---|---|
| | | Room (24° C.) | Fridge (8° C.) | Room (24° C.) | Fridge (8° C.) | Room (24° C.) | Fridge (8° C.) | Room (24° C.) | Fridge (8° C.) | Room (24° C.) | Fridge (8° C.) |
| 1 | FP Glass cartridges without preservative | CRS | CFS | 24rs | 24fs | 72rp | 72fp | 5rp | 5fp | 7rp | 7fp |

TABLE 1-continued

Microbiological examination of MDCs under study

| S.No S.No | Product studied MDCs | At 0 Hr just after first opening sent for MB-lab | | At 24 Hrs just after second opening sent for MB-lab | | At 72 Hrs just after Third opening sent for MB-lab | | On 5$^{th}$ day | | On 7$^{th}$ Day | |
|---|---|---|---|---|---|---|---|---|---|---|---|
| | | Room (24° C.) | Fridge (8° C.) | Room (24° C.) | Fridge (8° C.) | Room (24° C.) | Fridge (8° C.) | Room (24° C.) | Fridge (8° C.) | Room (24° C.) | Fridge (8° C.) |
| 2 | FP Glass cartridges with 1% Benzyl alcohol | CRS | CFS | 24rs | 24fs | 72rs | 72fs | 5rs | 5fs | 7rs | 7fs |
| 3 | FP Glass cartridges with 0.2% m-cresol | CRS | CFS | 24rs | 24fs | 72rs | 72fs | 5rs | 5fs | 7rs | 7fs |
| 4 | FP COP cartridges without preservative | CRS | CFS | 24rs | 24fs | 72rp | 72fp | 5rp | 5fp | 7rp | 7fp |
| 5 | FP-COP cartridges with 1% Benzyl alcohol | CRS | CFS | 24rs | 24fs | 72rs | 72fs | 5rs | 5fs | 7rs | 7fs |
| 6 | FP-COP cartridges with 0.2% M-cresol | CRS | CFS | 24rs | 24fs | 72rs | 72fs | 5rs | 5fs | 7rs | 7fs |

MDCs = Multi dose cartridges
CRS = control & sterile at room temperature
CFS = control & sterile in fridge
MB = Microbiology lab
fs = STERILE IN FRIDGE
rs = STERILE AT ROOM TEMPERATURE
fp = POSITIVE IN FRIDGE
rp = POSITIVE AT ROOM TEMPERATURE The results of the total 21 day study of the formulations in multiple dose containers with and without preservatives are as follows:

1) At '0' and '24' hour opening of the MDC, all the formulations have control and are sterile, when stored at 24° C. & 8° C.

2) On opening the MDC at 72 hours, and the 5th and 7th day, formulations comprising a preservative (benzyl alcohol or m-Cresol) showed control and sterility, when stored at 24° C. & 8° C. However, cartridges comprising formulations without preservative showed positive control at the same opening intervals.

The above study suggests that both COP and glass cartridges have the same log reduction and work effectively in controlling microbial contamination. However, a cartridge made of COP is more compatible with preservatives (benzyl alcohol & m-cresol) used in the tested formulations, has low protein & water absorption capacity, good chemical resistance, reduced shipping cost when compared to glass, thereby making it an ideal choice for delivering the formulations of the present invention.

In one preferred embodiment of the invention, the device for delivering pharmaceutical formulations of low molecular weight heparins or heparin-like compounds, is made of COP, such that said device is efficient in controlling impurities and microbial contamination when compared to device made of glass.

Compositions

In another embodiment, the present invention provides sterile, stable multiple dose pharmaceutical formulations comprising fondaparinux sodium and pharmaceutically acceptable excipients to be filled in cartridges made of COP for use in an injection device, for parenteral administration.

The pharmaceutical formulations may comprise fondaparinux sodium, one or more tonicity adjusting agent, optionally one or more preservatives, optionally one or more antioxidants, and water for injection.

Examples of suitable tonicity adjusting agents include, without limitation, sodium chloride, potassium chloride, dextrose, glycerol, mannitol, xylitol, anhydrous dextrose, amino acids (such as tryptophan, aspartic acid, threonine, arginine, lysine, etc.), polyethylene glycol (PEG-400), and ethyl alcohol. In preferred embodiments of the invention, the tonicity adjusting agent is sodium chloride.

Examples of suitable antioxidants include, without limitation ascorbic acid, sodium ascorbate, Butylated hydroxy toluene (BHT), Butylated hydroxy anisole, propyl gallate, sodium sulfite, sodium bisulfite, sodium metabisulfite, and tocopherol or derivatives thereof, metal chelating agents such as citric acid, ethylenediaminetetraacetic acid (EDTA), sorbitol, tartaric acid and the like. In preferred embodiments of the invention, the antioxidant is EDTA, BHT.

Examples of suitable preservatives include, without limitation, parabens (e.g., methyl paraben and propyl paraben), benzoic acid and its salts, other esters of parahydroxybenzoic acid such as butyl paraben, alcohols such as ethyl alcohol or benzyl alcohol, phenolic compounds such as phenol, or quaternary compounds such as benzalkonium chloride, mercury-containing substances such as merfen and thiomerosal, and stabilized chlorine dioxide. In preferred embodiments, the preservative is benzyl alcohol or m-cresol.

The pharmaceutical formulations may additionally comprise one or more pharmaceutically acceptable pH adjusting agents. Examples of suitable pH adjusting agents include, without limitation, acids such as acetic, boric, citric, lactic, phosphoric, and hydrochloric acids; bases such as sodium hydroxide, sodium phosphate, sodium borate, sodium citrate, sodium acetate, sodium lactate, trishydroxymethyl-amino-methane and the like. In preferred embodiments, the pH adjusting agents are sodium hydroxide and hydrochloric acid.

In one embodiment, the present invention provides sterile, stable, multiple dose formulations comprising fondaparinux sodium in a total dose range of about 2 mg to about 200 mg or more, having a pH in the range of about 5.0 to about 8.0, for use in an injection device.

In some embodiments, the present invention provides sterile, stable, multiple dose pharmaceutical formulations comprising fondaparinux sodium, sodium chloride, and water for injection to be filled in cartridges for use in multiple dose injection devices.

In other embodiments, the present invention provides sterile, stable, multiple dose pharmaceutical formulations comprising fondaparinux sodium, sodium chloride, benzyl alcohol, and water for injection to be filled in cartridges for use in multiple dose injection devices.

In some other embodiments, the present invention provides sterile, stable multiple dose pharmaceutical formulations comprising fondaparinux sodium, sodium chloride, m-cresol, and water for injection to be filled in cartridges for use in multiple dose injection devices.

In some embodiments, the present invention relates to sterile, stable multiple dose pharmaceutical formulations comprising fondaparinux sodium and one or more pharmaceutically acceptable excipients along with a small percentage of related oligosaccharides as impurities.

Fondaparinux sodium shares a similarity in chemical structure and physicochemical characteristics with related oligosaccharides, which cannot be eliminated satisfactorily by purification methods. Moreover, it has been observed that some of these products are readily degradable, when subjected to sterilization methods such as autoclaving and thus produce additional impurities. The impurities have been quantitatively identified by high performance liquid chromatography (HPLC) under the conditions in Table 2. The levels of various impurities in a test solution of fondaparinux packaged in a COP cartridge in comparison to the marketed form of Arixtra® are shown in Table 3.

TABLE 2

Chromatographic Conditions

| | |
|---|---|
| Mobile Phase A | 15 ± 10 ppm of DMSO in 5 mM $PO_4$ Solution |
| Mobile Phase B | 2M NaCl in 5 mM $PO_4$ |
| Flow rate | 1.0 mL/minute |
| Column | Thermo Scientific Carbopac PA1 Column (4*250 mm), Guard Column Carbopac PA1 (4*50 mm) |
| Column temperature | 25° C. |
| Injection volume | 100 μL |
| Detector wavelength | UV 210 nm |
| Run time | 50 minutes |
| Analytical HPLC | Dionex Ultimate 3000 |

Gradient program

| Time (minutes) | Solution (A) (%) | Solution (B) (%) |
|---|---|---|
| 0 | 55 | 45 |
| 5 | 55 | 45 |
| 25 | 5 | 95 |
| 30 | 5 | 95 |
| 35 | 55 | 45 |
| 50 | 55 | 45 |

TABLE 3

| Impurities analysed in Arixtra ® (Marketed Product) | | | Impurities analysed in Fondaparinux (Test formulation) | | |
|---|---|---|---|---|---|
| Impurity | Chemical name | Relative % (by HPLC area) | Impurity | Chemical name | Relative % (by HPLC area) |
| Comp A | | 0.6 | Comp A | | <LOD* |
| Comp B | Methyl-O-(4-deoxy-2-O-sulfo-a-L-threo-hex-4-enopyranosyluronate)-(1 ® 4)-O-(2-deoxy-6-O-sulfo-2-sulfamino-a-D-glucopyranoside), tetrasodium salt | 3.98 | Comp B | Methyl-O-(4-deoxy-2-O-sulfo-a-L-threo-hex-4-enopyranosyluronate)-(1 ® 4)-O-(2-deoxy-6-O-sulfo-2-sulfamino-a-D-glucopyranoside), tetrasodium salt | <LOD* |
| Comp C | .Methyl O-(2-deoxy-6-O-sulfo-2-(sulfoamino)-a-D-glucopyranosyl)-(1 ® 4)-O-(b-D-glucopyranosyluronate)-(1 ® 4)-O-(2-deoxy-3,6-di-O-sulfo-2-amino-a-D-glucopyranosyl-(1 ® 4)-O-2-O-sulfo-a-L-idopyranosyluronate)-(1 ® 4)-(2-deoxy-6-O-sulfo-2-(sulfoamino)-a-D-glucopyranoside), nonasodium salt. | 0.16 | Comp C | Methyl O-(2-deoxy-6-O-sulfo-2-(sulfoamino)-a-D-glucopyranosyl)-(1 ® 4)-O-(b-D-glucopyranosyluronate)-(1 ® 4)-O-(2-deoxy-3,6-di-O-sulfo-2-amino-a-D-glucopyranosyl-(1 ® 4)-O-2-O-sulfo-a-L-idopyranosyluronate)-(1 ® 4)-(2-deoxy-6-O-sulfo-2-(sulfoamino)-a-D-glucopyranoside), nonasodium salt. | <LOD* |

TABLE 3-continued

| Impurities analysed in Arixtra ® (Marketed Product) | | | Impurities analysed in Fondaparinux (Test formulation) | | |
|---|---|---|---|---|---|
| Impurity | Chemical name | Relative % (by HPLC area) | Impurity | Chemical name | Relative % (by HPLC area) |
| Comp D | | 0.14 | Comp D | | <LOD* |
| Comp E | | 0.32 | Comp E | | 0.37 |
| Comp F | | 0.39 | Comp F | | 0.67 |
| Comp G | .2-Deoxy-6-O-sulfo-2-(sulfoamino)-a-D-glucopyranosyl-(1 ® 4)-O-(b-D-glucopyranosyluronate)-(1 ® 4)-O-(2-deoxy-3,6-di-O-sulfo-2-(sulfoamino)-a-D-glucopyranosyl)-(1 ® 4)-O-(2-O-sulfo-a-L-idopyranosyluronate)-(1 ® 4)-(1,2-dideoxy-6-O-sulfo-2-(sulfoamino)-D-enoglucopyranoside), decasodium salt | 1.63 | Comp G | .2-Deoxy-6-O-sulfo-2-(sulfoamino)-a-D-glucopyranosyl-(1 ® 4)-O-(b-D-glucopyranosyluronate)-(1 ® 4)-O-(2-deoxy-3,6-di-O-sulfo-2-(sulfoamino)-a-D-glucopyranosyl)-(1 ® 4)-O-(2-O-sulfo-a-L-idopyranosyluronate)-(1 ® 4)-(1,2-dideoxy-6-O-sulfo-2-(sulfoamino)-D-enoglucopyranoside), decasodium salt | <LOD* |

Ref: Fondaparinux injection monograph USP38 3607.

The following impurities were identified by HPLC:
Impurity-B (Compound-B): Methyl-O-(4-deoxy-2-O-sulfo-a-L-threo-hex-4-enopyranosyluronate)-(1®4)-O-(2-deoxy-6-O-sulfo-2-sulfamino-a-D-glucopyranoside), tetrasodium salt.
Impurity-C(Compound-C): Methyl O-(2-deoxy-6-O-sulfo-2-(sulfoamino)-a-D-glucopyranosyl)-(1®4)-O-(b-D-glucopyranosyl uronate)-(1®4)-O-(2-deoxy-3,6-di-O-sulfo-2-amino-a-D-glucopyranosyl-(1®4)-O-2-O-sulfo-a-L-idopyranosyluronate)-(1®4)-(2-deoxy-6-O-sulfo-2-(sulfoamino)-a-D-glucopyranoside), nonasodium salt.
Impurity-G (Compound-G): 2-Deoxy-6-O-sulfo-2-(sulfoamino)-a-D-glucopyranosyl-(1®4)-O-(b-D-glucopyranosyluronate)-(1®4)-O-(2-deoxy-3,6-di-O-sulfo-2-(sulfoamino)-a-D-glucopyranosyl)-(1®4)-O-(2-O-sulfo-a-L-idopyranosyluronate)-(1®4)-(1,2-dideoxy-6-O-sulfo-2-(sulfoamino)-D-enoglucopyranoside), decasodium salt. The other impurities identified are Impurity-A, Impurity-D, Impurity-E and Impurity-F.

In one embodiment, the pharmaceutical formulations comprise about 98% of fondaparinux sodium, and impurity A. In preferred embodiments of the invention, the amount of the impurity A is below the level of detection.

In another embodiment, the pharmaceutical formulations comprise about 98% of fondaparinux sodium, and impurity B. In preferred embodiments of the invention, the amount of the impurity B is below the level of detection.

In yet another embodiment, the pharmaceutical formulations comprise about 98% of fondaparinux sodium, and impurity C. In preferred embodiments of the invention, the amount of the impurity C is below the level of detection.

In yet another embodiment, the pharmaceutical formulations comprise about 98% of fondaparinux sodium, and impurity D. In preferred embodiments of the invention, the amount of the impurity D is below the level of detection.

In another embodiment, the pharmaceutical formulations comprise about 98% of fondaparinux sodium, and about 0.4% or less of impurity E. In preferred embodiments of the invention, the amount of the impurity E is about 0.37%.

In another embodiment, the pharmaceutical formulations comprise about 98% of fondaparinux sodium, and about 0.7% or less of impurity F. In preferred embodiments of the invention, the amount of the impurity E is about 0.67%.

In another embodiment, the pharmaceutical formulations comprise about 98% of fondaparinux sodium, and impurity G. In preferred embodiments of the invention, the amount of the impurity G is below the level of detection.

In more preferred embodiments, the present invention provides sterile, stable, multiple dose pharmaceutical formulations for subcutaneous administration, comprising fondaparinux sodium to be filled in cartridges for use in a multiple dose injection device which is superior in terms of controlling impurity levels compared to marketed formulations in glass pre-filled syringes.

Another embodiment of the present invention provides methods for preparing sterile, multiple dose pharmaceutical formulations of fondaparinux sodium to be filled in cartridges for use in multiple dose injection devices.

In one embodiment, the present invention provides a method for preparing a sterile, stable, multiple dose formulation of fondaparinux sodium, wherein the method comprises: 1) dissolving a weighed quantity of fondaparinux sodium in sufficient volume of sodium chloride solution (for instance about 0.001 to 2% sodium chloride, preferably about 0.9%) in water for injection, 2) adjusting the pH if necessary to about 5.0 to about 8.0 using sodium hydroxide or hydrochloric acid, 3) adjusting the final volume using isotonic solution of NaCl in water for injection, 4) filtration of the final solution using nitrogen gas as filtration aid, and 5) aseptic filling followed by terminal sterilization.

In another embodiment of the invention the method for preparing a sterile, stable, multiple dose pharmaceutical formulation of fondaparinux sodium comprises: 1) preparing a first solution by dissolving the active substance in isotonic solution of sodium chloride, 2) preparing a second solution by dissolving a preservative in water for injection, 3) mixing the first and second solutions, 4) adjusting the pH of the mixture if necessary, 5) adjusting the final volume using water for injection, and 6) filtration followed by terminal sterilization.

The present invention also provides methods for filling the multiple dose formulations of fondaparinux sodium into the cartridges for use in injection devices. Conventional filling methods are well known to the persons skilled in the art and the use of such methods is included in the practice of this application. A suitable method may include online vacuum filling of the compositions followed by online vacuum stoppering.

EXAMPLES

Stability of pharmaceutical formulations of the present invention have been evaluated by long term and accelerated studies under ICH conditions as described below. The multiple dose pharmaceutical formulations comprising fondaparinux sodium according to the present invention were evaluated by appropriately accelerating the drug products at 40° C. for 3 months (90 days) and simultaneously analyzing the samples as per defined schedule for assay and organic impurities. Assay and organic impurities is important to the quality and stability of the product. Therefore evaluating and comparing the developed formulations with the above tests is justified. The test specifications are listed below in the table 4.

TABLE 4

| S. No | Test | Specification |
|---|---|---|
| 1.0 | Assay | Assay value should be between 95%-105% |
| 2.0 | Organic Impurities | 1. Related compound A(RRT 0.35)-NMT 1.0%<br>2. Related compound B (RRT 0.48)-NMT 0.150%<br>3. Related compound C (RRT 0.76)¬-NMT 0.8%<br>4. Related compound D (RRT 0.80)-NMT 0.8%<br>5. Related compound E (RRT 0.93)-NMT 0.15<br>6. Related compound F (RRT 1.29)-NMT 2.0%<br>7. Related compound G(RRT 1.34)-NMT 0.10%<br>8. Total degradation compound-NMT 5.0% |

Specified Impurities and Fondaparinux Related Substance:
Related Compound B; Methyl-O-(4-deoxy-2-O-sulfo-a-L-threo-hex-4-enopyranosyluronate)-(1→4)-O-(2-deoxy-6-O-sulfo-2-sulfamino-a-D-glucopyranoside), tetrasodium salt.
Related Compound C; Methyl O-(2-deoxy-6-O-sulfo-2-(sulfoamino)-a-D-glucopyranosyl)-(1→4)-O-(b-D-glucopyranosyluronate)-(1→4)-O-(2-deoxy-3,6-di-O-sulfo-2-amino-a-D-glucopyranosyl-(1→4)-O-2-O-sulfo-a-L-idopyranosyluronate)-(1→4)-(2-deoxy-6-O-sulfo-2-(sulfoamino)-a-D-glucopyranoside), nonasodium salt.
Related Compound G; 2-Deoxy-6-O-sulfo-2-(sulfoamino)-a-D-glucopyranosyl-(1→4)-O-(b-D-glucopyranosyluronate)-(1→4)-O-(2-deoxy-3,6-di-O-sulfo-2-(sulfoamino)-a-as D-glucopyranosyl)-(1→4)-O-(2-O-sulfo-a-L-idopyranosyluronate)-(1→4)-(1,2-dideoxy-6-O-sulfo-2-(sulfoamino)-D-enoglucopyranoside), decasodium. Salt.

The test methods for assay and organic impurities of fondaparinux sodium are based on Ion exchange chromatography. The chromatographic column employs Dionex Carbopac PA1 Column (4*250 mm) as a stationary phase and the detection is at 210 nm. Testing multiple dose formulations with Benzyl alcohol or m-cresol as preservatives will have interference in the background therefore the samples are pretreated by passing through reverse phase C18 Solid phase extraction cartridges. Nonionic preservative components in the sample interact with the stationary phase and the ionic analyte component in the sample passes through the cartridge. Flow-through was collected and loaded as the sample for analysis of Fondaparinux sodium injection.

The evaluation of multiple dose cartridge formulations was performed in two stages. In a first stage repeat dosing (0.5 mL) was performed on the same set of samples at day 0, 2, 4, 6, 8 and 10. At the second stage, product quality was tested at a pre-defined intervals (initial, 22nd, 45th and 90th day). In both the cases the samples were maintained at accelerated condition of storage (40° C.±3° C.). The study was planned and executed with single batch samples for each formulation. Samples were prepared based on the below mentioned details in Table 5.

TABLE 5

Test Formulations

| Formula No. | Formulation Name | Composition | Primary Packing |
|---|---|---|---|
| 1 | F1BACOP | Fondaparinux-12.5 mg<br>Nacl-0.75% (w/w)<br>Benzyl alcohol-1% (w/w) | Cartridge made of COP |
| 2 | F2MCCOP | Fondaparinux-12.5 mg<br>Nacl-0.75% (w/w)<br>m-Cresol-0.2% (w/w) | Cartridge made of COP |
| 3 | F3WOPCOP | Fondaparinux-12.5 mg<br>Nacl-0.75% (w/w) | Cartridge made of COP |

The results of assay and impurities over time for Formula 1 (Fondaparinux with benzyl alcohol) are shown below in Table 6.

TABLE 6

Multidose cartridge Formulation 1 evaluation results

| Formulation | F1BACOP | | | | | | | | |
|---|---|---|---|---|---|---|---|---|---|
| | $1^{st}$ dose | $2^{nd}$ dose | $3^{rd}$ dose | $4^{th}$ dose | $5^{th}$ dose | $6^{th}$ dose | | | |
| Test parameters / Specification | or 0 day | or $2^{nd}$ day | or $4^{th}$ day | or $6^{th}$ day | or $8^{th}$ day | or $10^{th}$ day | $22^{nd}$ day | 45 day | 90 day |
| Assay / Assay value should be between 95%-105%. | 99.9 | 99.86 | 99.82 | 99.6 | 99.82 | 99.72 | 98.71 | 98.68 | 98.26 |
| Organic Impurities / Related compound A (RRT 0.35)-NMT 1.0% | — | — | — | — | — | — | — | — | — |

TABLE 6-continued

Multidose cartridge Formulation 1 evaluation results

F1BACOP

| Test parameters | Formulation Specification | 1st dose or 0 day | 2nd dose or 2nd day | 3rd dose or 4th day | 4th dose or 6th day | 5th dose or 8th day | 6th dose or 10th day | 22nd day | 45 day | 90 day |
|---|---|---|---|---|---|---|---|---|---|---|
| | Related compound B (RRT 0.48)- NMT 0.150% | — | — | — | — | 0.06 | 0.09 | 0.2 | 0.8 | 0.86 |
| | Related compound C (RRT 0.76)- NMT 0.8% | — | — | — | — | — | — | — | — | — |
| | Related compound D (RRT 0.80)- NMT 0.8% | — | — | — | — | — | — | — | — | 0.62 |
| | Related compound E (RRT 0.93)- Identify | D | D | D | D | D | D | D | D | D |
| | Related compound F (RRT 1.29)- NMT 2.0% | 0.04 | 0.06 | 0.06 | 0.06 | 0.06 | 0.09 | 0.4 | 0.82 | 0.93 |
| | Related compound G (RRT 1.34)- NMT 0.10% | — | — | — | — | — | — | — | 0.02 | — |
| | Total degradation compound- NMT 5.0% | 0.04 | 0.06 | 0.06 | 0.06 | 0.12 | 0.18 | 0.6 | 1.64 | 2.41 |

The results of assay and impurities over time for Formula 2 (Fondaparinux with m-Cresol) are shown below in Table 7.

TABLE 7

Multidose cartridge Formulation 2 evaluation results

F2MCCOP

| Test parameters | Formulation Specification | 1st dose or 0 day | 2nd dose or 2nd day | 3rd dose or 4th day | 4th dose or 6th day | 5th dose or 8th day | 6th dose or 10th day | 22nd day | 45 day | 90 day |
|---|---|---|---|---|---|---|---|---|---|---|
| Assay | Assay value should be between 95%-105%. | 99.73 | 99.70 | 98.92 | 98.90 | 98.42 | 97.68 | 97.41 | 96.82 | 96.31 |
| Organic Impurities | Related compound A (RRT 0.35)- NMT 1.0% | — | — | — | — | — | | 0.92 | 0.86 | 1.23 |
| | Related compound B (RRT 0.48)- NMT 0.150% | — | — | — | — | 2.8 | 3.2 | 5.2 | 6.8 | 7.4 |
| | Related compound C (RRT 0.76)- NMT 0.8% | — | — | — | 0.26 | 0.53 | 0.59 | 0.73 | 1.14 | 1.25 |
| | Related compound D (RRT 0.80)- NMT 0.8% | — | — | 0.12 | 0.18 | 0.21 | 0.26 | 0.64 | 0.86 | 0.92 |

TABLE 7-continued

Multidose cartridge Formulation 2 evaluation results

| | | F2MCCOP | | | | | | | | |
|---|---|---|---|---|---|---|---|---|---|---|
| | Formulation | 1st dose | 2nd dose | 3rd dose | 4th dose | 5th dose | 6th dose | | | |
| Test parameters | Specification | or 0 day | or 2nd day | or 4th day | or 6th day | or 8th day | or 10th day | 22nd day | 45 day | 90 day |
| | Related compound E (RRT 0.93)-Identify | D | D | D | D | D | D | D | D | D |
| | Related compound F (RRT 1.29)-NMT 2.0% | 0.06 | 0.06 | 0.24 | 0.65 | 0.32 | 0.45 | 0.91 | 1.6 | 1.86 |
| | Related compound G (RRT 1.34)-NMT 0.10% | — | — | — | — | 0.21 | 0.26 | 0.34 | 0.43 | 0.52 |
| | Total degradation compound-NMT 5.0% | 0.06 | 0.06 | 0.36 | 1.09 | 4.07 | 4.76 | 7.82 | 11.69 | 11.32 |

The results of assay and impurities over time for Formula 3 (Fondaparinux without preservative) are shown below in Table 8.

TABLE 8

Multidose cartridge Formulation 3 evaluation results

| | | F3WOPCOP | | | | | | | | |
|---|---|---|---|---|---|---|---|---|---|---|
| | Formulation | 1st dose | 2nd dose | 3rd dose | 4th dose | 5th dose | 6th dose | | | |
| Test parameters | Specification | or 0 day | or 2nd day | or 4th day | or 6th day | or 8th day | or 10th day | 22nd day | 45 day | 90 day |
| Assay | Assay value should be between 95%-105%. | 99.70 | 98.98 | 98.64 | 98.54 | 97.06 | 96.91 | 96.84 | 96.12 | 95.86 |
| Organic Impurities | Related compound A (RRT 0.35)-NMT 1.0% | — | — | — | — | — | — | 1.6 | 1.6 | 1.84 |
| | Related compound B (RRT 0.48)-NMT 0.150% | — | 0.02 | 0.05 | 0.05 | 6.95 | 7 | 7.2 | 8.3 | 8.6 |
| | Related compound C (RRT 0.76)-NMT 0.8% | — | — | 0.13 | 0.23 | 0.48 | 0.56 | 0.84 | 0.26 | — |
| | Related compound D (RRT 0.80)-NMT 0.8% | — | 0.43 | 0.42 | 0.56 | 0.65 | 0.65 | 0.52 | 1.28 | 0.96 |
| | Related compound E (RRT 0.93)-Identify | D | D | D | D | D | D | D | D | D |
| | Related compound F (RRT 1.29)-NMT 2.0% | 0.06 | 0.09 | 0.09 | 0.42 | 0.86 | 0.81 | 1.4 | — | 2.6 |
| | Related compound G (RRT 1.34)-NMT 0.10% | — | 0.02 | 0.02 | 0.28 | 0.31 | 0.3 | 0.6 | 1.6 | 1.86 |

TABLE 8-continued

Multidose cartridge Formulation 3 evaluation results

| Formulation | Test parameters | Specification | F3WOPCOP | | | | | | | | |
|---|---|---|---|---|---|---|---|---|---|---|---|
| | | | 1st dose or 0 day | 2nd dose or 2nd day | 3rd dose or 4th day | 4th dose or 6th day | 5th dose or 8th day | 6th dose or 10th day | 22nd day | 45 day | 90 day |
| | Total degradation compound- NMT 5.0% | | 0.06 | 0.13 | 0.71 | 1.54 | 9.25 | 9.32 | 12.16 | 11.44 | 15.86 |

*D = Detected

Overlay chromatogram comparisons of each formulation are shown in FIGS. 2-8. When comparing the stability data of Formulation 1 and Formulation 2 with Formulation 3 there is a definite increase in degradation products in Formulation 3 as time goes on. Further, when evaluating Formulation 1 and Formulation 2, multi-dose Formulation 1 is more stable in the defined study period. The assay and Impurities are within the limits. Formulation 2 with m-cresol preservative in COP packing is not as stable as Formulation 1. Observed assay data indicates out of trend values (OOT) and in Formulation 2 there is a quantitative increase in the degradation of products and the few degradation Impurities values are out of specification.

In one embodiment, the multiple dose pharmaceutical formulations of the present invention were found to show no significant degradation when stored at 25° C. at 60% RH for a period of about 24 months.

In another embodiment, the multiple dose pharmaceutical formulations of the present invention were found to show no significant degradation when stored at 30° C. at 60% RH for a period of about 12 months.

In yet another embodiment, the multiple dose pharmaceutical formulations of the present invention were found to show no significant degradation when stored at 40° C. at 75% RH for a period of about 6 months.

In some embodiments, the present invention provides sterile, stable multiple dose pharmaceutical formulations of fondaparinux sodium to be filled in cartridges which maintain their physical and chemical characteristics over a period of 24 months when stored at a temperature of 25° C. and 60% relative humidity.

In further embodiments, the present invention provides sterile, stable multiple dose pharmaceutical formulations of fondaparinux sodium filled in cartridges for the prophylaxis and treatment of thromboembolic diseases, namely acute deep vein thrombosis and acute pulmonary embolism, for subcutaneous injection to a subject in need thereof.

In further embodiments, the invention may include, but is not limited to, forms of packaging for active pharmaceutical ingredients, to provide stability during storage and transportation. In some embodiments, the package or dispenser device is accompanied by instructions for administration, such as instructions for administering the compounds or compositions for treating a disease.

Without being limited by theory, the device of the present invention may be advantageously used to deliver low molecular weight heparins or heparin-like molecules such as fondaparinux. The device and the delivery of the drug through the device are such that it prevents the disadvantages of the prior art. It is envisaged that by providing low molecular weight heparins in cartridges of the present invention, the shelf life or stability of the product is enhanced and the impurity content of the product is decreased, thereby contributing to the overall efficacy of the product. The device of the present invention is convenient to use by the end users and eliminates dosing error. Furthermore, the device and the method of delivery of low molecular weight heparins using the device of the present invention reduces the medication cost, is economic for the end user, reduces drug waste, minimizes hospital and industrial waste and eliminates risk of microbial contamination.

The foregoing embodiments and advantages are merely exemplary and are not to be construed as limiting the scope of the present invention. The description of the exemplary embodiments of the present invention is intended to be illustrative and not to limit the scope of the invention. Various modifications, alterations and variations, which are apparent to a person skilled in the art, are intended to fall within the scope of the invention.

What is claimed is:

1. A device comprising a multiple dose cartridge made of cyclo-olefin polymer (COP), the cartridge filled with low molecular weight heparins selected from the group consisting enoxaparin, ardeparin, dalteparin, fondaparinux, combinations thereof, and pharmaceutically acceptable salts thereof, the cartridge comprising a housing assembly, the housing assembly comprising a drug reservoir area, a narrowed neck area, and a plunger, wherein the housing assembly is made of COP.

2. The device of claim 1 filled with fondaparinux or a pharmaceutically acceptable salt thereof.

3. The device of claim 1 which is for delivering successive individual dosages of fondaparinux or a pharmaceutically acceptable salt thereof, that is superior in mechanical properties and controlling microbial contamination compared to a device made of glass.

4. A device in the form of a multiple dose cartridge made of cyclo-olefin polymer (COP) comprising a housing assembly, the housing assembly made of a material and comprising a drug reservoir area and a plunger, wherein the material of the housing assembly consists of COP, the cartridge sealed at one end using a disc and a cap, wherein the cartridge is filled with fondaparinux or a pharmaceutically acceptable salt thereof.

5. The device of claim 4, further comprising a composition that is a sterile, stable multiple dose pharmaceutical formulation for subcutaneous administration, comprising fondaparinux sodium, the device configured for use in a multiple dose injection instrument.

6. A cyclo-olefin polymer (COP) device comprising a housing assembly comprising a drug reservoir area and a plunger, wherein the housing assembly is made of COP, and wherein the drug reservoir area contains a multiple dose fondaparinux composition which is stable for a period of 3 months at accelerated storage conditions.

7. A sterile, stable, multiple dose filled cartridge for subcutaneous administration comprising fondaparinux sodium contained in a cartridge configured for use in a multiple dose injection device, the cartridge comprising a housing assembly comprising a drug reservoir area and a plunger, wherein the housing assembly is made of cyclo-olefin polymer.

8. The multiple dose filled cartridge of claim 7, further comprises a pharmaceutically acceptable tonicity adjusting agent.

9. The multiple dose filled cartridge of claim 7, further comprises one or more pharmaceutically acceptable excipients selected from the group consisting of preservatives, antioxidants, or combinations thereof.

10. The multiple dose filled cartridge of claim 9, wherein the one or more pharmaceutically acceptable excipients comprise a pharmaceutically acceptable preservative, and the pharmaceutically acceptable preservative is selected from the group consisting of benzyl alcohol, methyl paraben, propyl paraben, m-cresol, and of combinations thereof.

11. The multiple dose filled cartridge of claim 9, wherein the antioxidant is ethylenediaminetetraacetic acid (EDTA) or butylated hydroxytoluene (BHT).

12. The multiple dose filled cartridge of claim 7, further comprising about 98% fondaparinux sodium and one or more related impurities.

13. The multiple dose of claim 7, further comprising Impurity-A, Impurity-B, Impurity-C, Impurity-D, and Impurity-G below the level of detection as measured by HPLC, which remains stable for a period of 24 months on storage at 25° C. and 60% relative humidity.

14. The multiple dose filled cartridge of claim 7, comprising about 98% of fondaparinux sodium along with Impurity-A, Impurity-B, Impurity-C, Impurity-D, and Impurity-G below the level of detection as measured by HPLC, which remains stable for a period of 24 months on storage at 25° C. and 60% relative humidity.

* * * * *